United States Patent [19]

Büchel et al.

[11] 4,053,616

[45] Oct. 11, 1977

[54] COMBATING RUST FUNGI WITH 1-[1',2',4'-TRIAZOLYL-(1')]-1-(4'-PHENYL-PHENOXY)-3,3-DIMETHYL-BUTAN-2-ONE

[75] Inventors: Karl Heinz Büchel; Wolfgang Krämer, both of Wuppertal; Wilhelm Brandes, Cologne; Paul-Ernst Frohberger, Leverkusen, all of Germany

[73] Assignee: Bayer Aktiengesellschaft, Leverkusen, Germany

[21] Appl. No.: 586,122

[22] Filed: June 11, 1975

[30] Foreign Application Priority Data

June 28, 1974 Germany .................... 2431073

[51] Int. Cl.² ............................................ A01N 9/22
[52] U.S. Cl. ................................................ 424/269
[58] Field of Search ..................................... 424/269

[56] References Cited

U.S. PATENT DOCUMENTS 3,912,752  10/1975  Meiser et al. .................. 424/269

OTHER PUBLICATIONS

Chemical Abstracts, vol. 79 (1973), p. 105257y.

*Primary Examiner*—V. D. Turner
*Attorney, Agent, or Firm*—Burgess, Dinklage & Sprung

[57] ABSTRACT

The compound 1-[1, 2, 4 -triazolyl-(1')]-1-(4'-phenyl-phenoxy)-3,3-dimethyl-butan-2-one of the formula (I),

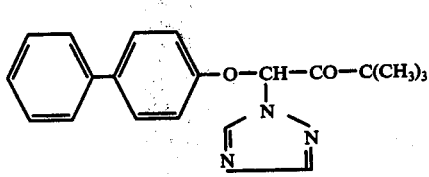

has a particularly good selective fungicidal activity against rust fungi.

5 Claims, No Drawings

COMBATING RUST FUNGI WITH 1-[1',2',4'-TRIAZOLYL-(1')]-1-(4'-PHENYL-PHENOXY)-3,3-DIMETHYL-BUTAN-2-ONE

The present invention relates to and has for its objects the selective combating of rust fungi with 1-[1,2,4-triazolyl-(1)]-1-(4'-phenyl-phenoxy)-3,3-dimethyl-butan-2-one, and active compositions in the form of mixtures of such compound with solid and liquid dispersible carrier vehicles, with other and further objects becoming apparent from a study of the within specification and accompanying examples.

It has been disclosed in German Published Specification DOS No. 2,201,063 that certain 1,2,4-triazolyl derivatives, such as, for example, 1-[1,2,4-triazolyl-(1)]-1-(4-chlorophenoxy)-3,3-dimethylbutan-2-one (Compound A), possess a very good fungicidal activity. However, nothing is known of the activity against rust fungi, which is of interest from a commercial point of view. The same remark also applies to similar compounds which, from U.S. Pat. No. 3,321,366 and German Published Specification DOS No. 1,795,249, are known in general terms to have a good fungicidal activity, such as, for example, triphenylmethyl-imidazolyl and triazolyl derivatives.

It has been found that the known compound 1-[1,2,4-triazolyl-(1)]-1-(4'-phenyl-phenoxy)-3,3-dimethylbutan-2-one, which has the formula

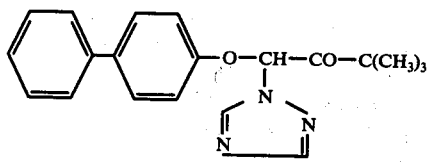

(I)

has a particularly good selective fungicidal activity against rust fungi.

Surprisingly, 1-[1,2,4-triazolyl-(1)]-1-(4'-phenyl-phenoxy)-3,3-dimethylbutan-2-one shows a substantially greater selective fungicidal action than the comparable triazole derivatives known from the state of the art, such as, for example, 1-[1,2,4-triazolyl-(1)]-1-(4'-chlorophenoxy)-3,3-dimethylbutan-2-one. The use of the active compound in accordance with this invention thus represents an enrichment of the art.

The compound of the formula (I) to be used according to the invention has been disclosed in German Published Specification DOS No. 2,201,063, as has its preparation by four different processes. Thus, for example, the compound is obtained when 1-chloro-1-(4'-phenyl-phenoxy)-3,3-dimethylbutan-2-one is reacted with excess 1,2,4-triazole in a polar organic solvent in the presence of an inorganic acid-binding agent, preferably at 80° to 120° C, as shown in Example 1(C) hereinbelow.

The active compound to be used according to the invention not only possesses powerful fungitoxic properties but also does not damage crop plants in the concentrations required to combat the harmful fungi. For these reasons, it is suitable for use as a plant protection agent for combating fungi.

Fungitoxic agents are employed in plant protection for combating *Archimycetes, Phycomycetes, Ascomycetes, Basidiomycetes* and *Fungi Imperfecti.*

The active compound according to the invention displays a particularly good activity against rust fungi from the genera *Uromyces* and *Puccinia,* for example against *Uromyces phaseoli,* the pathogen of bean rust, and against *Puccinia recondita,* the pathogen of leaf rust of wheat.

A fact to be emphasised is that the active compound displays not only a protective action but also a curative action, that is to say that it is active when used after contamination of the host plant by the spores of the fungus.

The active compound to be used according to the invention has only a low toxicity to warm-blooded animals and, because of its low odor and its toleration by human skin, it is not unpleasant to handle.

The active compound according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, suspensions, emulsifiable concentrates, spray powders, pastes, soluble powders, dusting agents, granules, etc. These are prepared in known manner, for instance by extending the active compound with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as freon; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkanes (e.g. cyclohexane, etc.), paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone methyl isobutyl ketone, cyclohexanone, etc.), and/or water; as well as inert dispersible finely divided solid carriers, such as ground natural minerals (e.g. kaolins, clays, alumina, silica, chalk, i.e. calcium carbonate, talc, attapulgite, montmorillonite, kieselguhr, etc.) and ground synthetic minerals (e.g. highly dispersed silicic acid, silicates, e.g. alkali silicates, etc.); whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents, such as lignin, sulfite waste liquors, methyl cellulose, etc.

Such active compound may be employed alone or in the form of mixtures with one another and/or with such solid and/or liquid dispersible carrier vehicles and/or with other known compatible active agents, especially plant protection agents, such as other fungicides, or insecticides, acaricides, nematocides, bactericides, rodenticides, herbicides, fertilizers, growth-regulating agents, bird repellents, agents for improving soil structure, etc., if desired, or in the form of particular dosage preparations for specific application made therefrom, such as solutions, emulsions, suspensions, powders, pastes and granules which are thus ready for use.

As concerns commercially marketed preparations, these generally contemplate carrier composition mixtures in which the active compound is present in an amount substantially between about 0.1-95% by weight, and preferably 0.5-90% by weight, of the mixture, whereas carrier composition mixtures suitable for direct application or field application generally contemplate those in which the active compound is present in an amount substantially between about 0.0001-10%, preferably 0.01-1%, by weight of the mixture. Thus, the present invention contemplates over-all compositions which comprise mixtures of a conventional dispersible carrier vehicle such as (1) a dispersible inert finely divided carrier solid, and/or (2) a dispersible carrier liquid such as an inert organic solvent and/or water preferably including a surface-active effective amount of a carrier vehicle assistant e.g. a surface-active agent, such as an emulsifying agent and/or a dispersing agent, and an amount of the active compound which is effective for the purpose in question and which is generally between about 0.0001-95%, and preferably 0.01-95%, by weight of the mixture.

The active compound can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50-100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20-100% by weight of the active compound. Especially when used as a leaf fungicide, the active-compound concentration in the use forms can be varied within a fairly wide range. It is in general between 0.1 and 0.00001 percent by weight, preferably between 0.05 and 0.0001 percent.

When treating seed, an amount of active compound of 0.001 to 50 g per kilogram of seed is generally required, preferably 0.01 to 10 g.

Furthermore, the present invention contemplates methods of selectively killing, combating or controlling pests, e.g. fungi, and more particularly methods of combating rust fungi, which comprises applying to at least one of correspondingly (a) such fungi and (b) the corresponding habitat thereof, i.e. the locus to be protected, e.g. to a growing crop, to an area where a crop is to be grown or to a domestic animal, a correspondingly combative or toxic amount, i.e. a fungicidally effective amount, of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, dressing, encrusting, and the like.

It will be realized, of course, that the concentration of the particular active compound utilized in admixture with the carrier vehicle will depend upon the intended application. Therefore, in special cases it is possible to go above or below the aforementioned concentration ranges.

The unexpected superiority and outstanding activity of the particular compound of the present invention are illustrated, without limitation, by the following examples:

EXAMPLE 1 a. 510 g (3 moles) of 4-hydroxybiphenyl were dissolved in 3 l of methyl ethyl ketone. 390 g of ground potassium carbonate were added and the mixture was heated to 80° C. 405 g (3 moles) of α-chloropinacoline were added dropwise over the course of 2 hours and the mixture was then stirred for a further 15 hours at 80° C. After cooling, it was filtered and the filter residue was rinsed with methyl ethyl ketone. The resulting filtrate was concentrated to dryness in vacuo by distilling off the solvent. The residue was taken up in methylene chloride and the solution was washed with 10% strength sodium hydroxide solution and twice with water, dried over sodium sulfate and concentrated in vacuo by distilling off the solvent. The residue was distilled, using a condenser cooled with hot water (50° C), to avoid crystallization. After a small amount of first runnings of chloropinacoline at 40° C/0.4 mm Hg, 658 g (82% of theory) of 1-(4'-phenyl-phenoxy)3,3-dimethylbutan-2-one were obtained at 170° to 180° C/0.4 mm Hg.

b. 1,292 g (4.83 moles) of 1-(4'-phenyl-phenoxy)-3,3-dimethylbutan-2-one were dissolved in 2.5 l of methylene chloride and 400 ml (4.9 moles) of sulfuryl chloride were added dropwise at the boil. The mixture was heated under reflux for 15 hours and was then concentrated by distilling off the solvent. After adding 250 ml of carbon tetrachloride, the solvent was again distilled off under a water-pump vacuum (bath temperature 65° C). Crude 1-chloro-1-(4'-phenyl-phenoxy)-3,3-dimethylbutan-2-one was obtained quantitatively, and was used further in the form obtained.

c) 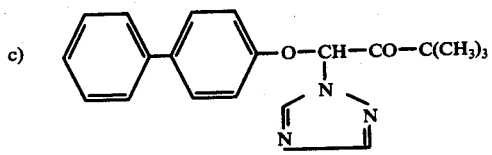 (I)

605 g (2 moles) of crude 1-chloro-1-(4'-phenyl-phenoxy)-3,3-dimethylbutan-2-one were dissolved in 1 liter of methyl ethyl ketone. This solution was added dropwise over the course of 3 hours at 15° to 20° C (slight cooling) to a suspension of 210 g (3 moles) of 1,2,4-triazole and 280 g (2 moles) of ground potassium carbonate in 2.5 l of methyl ethyl ketone. The mixture was stirred for 15 hours at room temperature and was then additionally heated under reflux for about 4 hours. After cooling, the mixture was filtered and the filter residue was rinsed with methyl ethyl ketone. The filtrate was concentrated by evaporation in vacuo and the residue was dissolved in methylene chloride, repeatedly washed with water and dried over sodium sulfate. After concentration in a water-pump vacuum, a crystalline substance was obtained, which was taken up in 1 liter of carbon tetrachloride and heated for 1 hour under reflux. Insoluble matter was filtered off hot (59.4 g of symmetrical isomer of melting point 185°–190° C) and the filtrate was left to crystallize. The crystals were filtered off and dried at 50° C. 430 g (64% of theory) of 1-[1, 2, 4 -triazolyl-(1 )]-1-(4'-phenyl-phenoxy)-3,3-dimethylbutan-2-one of melting point 105° to 108° C were obtained, the degree of purity being 95%.

0% denotes no attack and 100% denotes that the attack was as great as in the case of the control plants.

The active compounds, active-compound concentrations and results can be seen from the table which follows:

Table 1

Uromyces test/protective

| Active Compound | Infection in % of the infection of the untreated control at an active compound concentration (in %) of 0.00156 |
| --- | --- |
| (A) 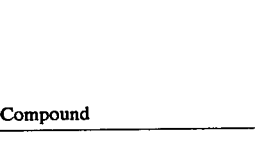 (comparison) | 91 |
| (I) 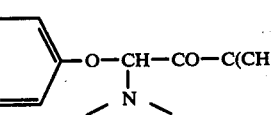 | 0 |

EXAMPLE 2

Uromyces test (bean rust)/protective.
Solvent: 4.7 parts by weight of acetone.
Emulsifier: 0.3 part by weight of alkylaryl polyglycol ether.
Water: 95 parts by weight.

The amount of active compound required for the desired concentration of active compound in the spray liquor was mixed with the stated amount of solvent and the concentrate was diluted with the stated amount of water which contained the stated additives.

Young bean plants, which were in the two-leaf stage, were sprayed with the spray liquor until dripping wet. The plants remained in a greenhouse for 24 hours at 20° to 22° C and a relative atmospheric humidity of 70% in order to dry. They were then inoculated with an aqueous uredospore suspension of the pathogen of bean rust (Uromyces phaseoli) and incubated for 24 hours in a dark humidity chamber at 20° to 22° C and 100% relative atmospheric humidity.

The plants were then set up in intense light in a greenhouse for 9 days at 20° to 22° C and a relative atmospheric humidity of 70 to 80%.

10 days after the inoculation, the infection of the plants was determined in % of the untreated, but also inoculated, control plants.

EXAMPLE 3

Uromyces test (bean rust)/curative.
Solvent: 4.7 parts by weight of acetone.
Emulsifier: 0.3 part by weight of alkylaryl polyglycol ether.
Water: 95 parts by weight.

The amount of active compound required for the desired active compound concentration in the spray liquor was mixed with the stated amount of the solvent and the concentrate was diluted with the stated amount of water, which contained the stated emulsifier.

Young bean plants which were in the 2-leaf stage were inoculated with an aqueous uredospore suspension of the pathogen of bean rust (Uromyces phaseoli) and incubated for 24 hours in a dark humidity chamber at 20° to 22° C and 100% relative atmospheric humidity. The plants were then transferred to a greenhouse where they dried.

After the appropriate dwell time, the plants were sprayed with the spray liquor, which had been prepared in the manner stated above, until they were dripping wet. They were then set up in intense light in a greenhouse at 20° to 22° C and a relative atmospheric humidity of 70 to 80%. 10 days after the inoculation, the infection of the bean plants was determined in percent of the untreated, but also inoculated, control plants.

0% denotes no infection and 100% denotes that the infection was as great as in the case of the control plants.

The active compounds, the active-compound concentrations, the dwell time between inoculation and spraying, and the results can be seen from the table which follows:

Table 2

| Active Compound | | Dwell time in hours: 24 | Infection in % of the infection of the untreated control at an active compound concentration (in %) of 0.0125 |
|---|---|---|---|
| 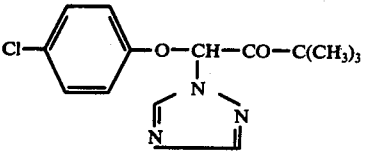 (comparison) | (A) | | 25 |
| 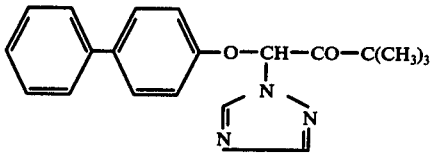 | (I) | | 0 |

EXAMPLE 4

Shoot treatment test/cereal rust (leaf-destructive mycosis)

To produce a suitable preparation of active compound, 0.25 part by weight of active compound was taken up in 25 parts by weight of dimethylformamide and 0.06 part by weight of emulsifier (alkylaryl polyglycol ether) and then 975 parts by weight of water were added. The concentrate was diluted with water to the desired final concentration of the spray liquor.

To test for protective activity, single leaved young wheat plants of the Michigan Amber variety were inoculated with a uredospore suspension of *Puccinia recondita* in 0.1% strength aqueous agar. After the spore suspension had dried on, the wheat plants were sprayed with the preparation of active compound until dew-moist and were placed in a greenhouse to incubate for 24 hours at about 20° C and 100% atmospheric humidity.

To test the curative activity, a corresponding procedure was followed except that the treatment of the wheat plants with the preparation of active compound was only carried out 48 hours after the inoculation, when the infection was already manifest.

After 10 days' dwell time of the plants at a temperature of 20° and 80–90% atmospheric humidity the occurrence of rust pustules on the plants was evaluated. The degree of infection was expressed as a percentage of the infection of the untreated control plants. 0% denotes no infection and 100% denotes the same degree of infection as in the case of the untreated control. The lower the degree of rust infection, the more active is the compound.

The active compounds, active-compound concentrations in the spray liquor and degrees of infection can be seen from the tables which follow.

Table 3

Shoot treatment test/cereal rust/protective

| Active compounds | | Active compound concentration in the spray liquor in % by weight | Infection in % of the untreated control |
|---|---|---|---|
| untreated | | — | 100.0 |
| 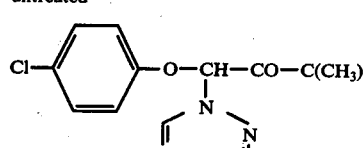 (comparison) | (A) | 0.01 | 32.5 |
| | | 0.005 | 75.0 |
| 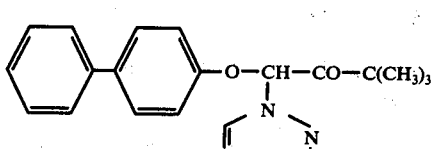 | (I) | 0.01 | 10.7 |
| | | 0.005 | 16.9 |
| | | 0.0025 | 28.8 |

Table 4

Shoot treatment test/cereal rust/curative

| Active compounds | | Active compound concentration in the spray liquor in % by weight | Infestion in % of the untreated control |
|---|---|---|---|
| untreated | | — | 100.0 |
| Cl—⟨benzene⟩—O—CH(triazole)—CO—C(CH₃)₃ (comparison) | A | 0.025<br>0.01<br>0.005 | 0.0<br>0.0<br>12.5 |
| ⟨biphenyl⟩—O—CH(triazole)—CO—C(CH₃)₃ | I | 0.025<br>0.05<br>0.005 | 0.0<br>0.0<br>0.0 |

It will be appreciated that the instant specification and examples are set forth by way of illustration and not limitation, and that various modifications and changes may be made without departing from the spirit and scope of the present invention.

What is claimed is:

1. A method of combating rust fungi of the genus Uromyces and Puccinia which comprises applying to the rust fungi or to seed a rust fungicidally effective amount of the compound of the formula

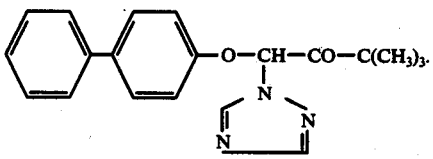

2. A method according to claim 1, in which the compound is applied as a composition containing it in about 0.1 to 0.00001 percent by weight.

3. A method according to claim 1, in which the active compound is applied to seed in an amount of about 0.001 to 50 g per kilogram of seed.

4. A method according to claim 1, in which the compound is applied to rust fungi of the genus Uromyces.

5. A method according to claim 1, in which the compound is applied to rust fungi of the genus Puccinia.

* * * * *